United States Patent [19]

Loewenthal

[11] Patent Number: 5,096,420
[45] Date of Patent: Mar. 17, 1992

[54] PERIODONTAL PROBE

[76] Inventor: Bernard Loewenthal, 51 Heights Rd., Stratham, N.H. 03885

[21] Appl. No.: 620,636

[22] Filed: Dec. 3, 1990

[51] Int. Cl.⁵ .............................................. A61C 19/04
[52] U.S. Cl. ....................................................... 433/72
[58] Field of Search .................................... 433/72, 75

[56] References Cited

U.S. PATENT DOCUMENTS

| | | | |
|---|---|---|---|
| 3,388,473 | 6/1968 | Loran | 433/102 |
| 3,855,705 | 12/1974 | Malmin | 433/102 |
| 3,935,640 | 2/1976 | Cohan | 433/75 |
| 4,203,223 | 5/1980 | Lautenschlager et al. | 433/75 |
| 4,340,069 | 7/1982 | Yeaple | 128/776 |
| 4,364,730 | 12/1982 | Axelsson | 433/141 |
| 4,445,857 | 5/1984 | Borst | 433/75 |
| 4,501,555 | 2/1985 | Ditchburn | 433/29 |
| 4,552,531 | 11/1985 | Martin | 433/147 |
| 4,768,952 | 9/1988 | Loewenthal | 433/72 |
| 4,791,940 | 12/1988 | Hirschfeld et al. | 433/72 |
| 4,886,454 | 12/1989 | Loewenthal et al. | 433/72 |
| 4,995,403 | 2/1991 | Beckman et al. | 433/72 |

FOREIGN PATENT DOCUMENTS

| | | |
|---|---|---|
| 84301673.4 | 9/1984 | European Pat. Off. |
| 2230327 | 12/1974 | France |
| 2086232A | 10/1981 | United Kingdom |

OTHER PUBLICATIONS

Photocopy of probe sold by Pro-Dentec, P.O. Box 4125, Batesville, Arkansas 72503.
"Hu-Friedy" catalog, p. 4.

*Primary Examiner*—John J. Wilson
*Attorney, Agent, or Firm*—Foley & Lardner

[57] ABSTRACT

A dental probe is disclosed for use in detecting periodontal disease and gingivitis. The probe includes an elongate member having a distal end with a tapered tip thereon; the distal end has a first portion indicating a non-diseased condition, a second portion indicating a moderately-diseased condition, and a third portion indicating a diseased condition where surgery is required, the first portion being disposed between the tip of the distal end and the second portion, the second portion being disposed between the first portion and the third portion, the third portion being disposed adjacent to the second portion. There is a narrow line defining a boundary between the areas, a first area indicating a diseased condition likely not requiring surgery located between the first portion and the narrow line and a second area indicating a diseased condition likely to require surgery located between the narrow line and the third portion. The invention also includes a method using the periodontal probe for diagnosing periodontal disease and gingivitis.

35 Claims, 2 Drawing Sheets

NORMAL

DISEASED SURGERY NOT LIKELY REQUIRED

DISEASED SURGERY LIKELY REQUIRED

DISEASED SURGERY REQUIRED

PERIODONTAL PROBE

CROSS REFERENCE

Reference is made to U.S. Pat. Nos. 4,768,952 and 4,886,454, which are hereby incorporated by reference.

BACKGROUND OF THE INVENTION

1. Field of the Invention

This invention relates to a periodontal probe. In particular, this invention relates to a periodontal probe having a calibrated tip for diagnosing periodontal disease and gingivitis.

2. Description of the Related Art

Periodontal disease is the most widespread disease in the world. It is basically an inflammatory disease of the gums which spreads to and destroys the supporting bone of the teeth. In time, teeth may abscess, become loose or painful and either fall out or are removed by a dentist. Fortunately, the dental profession has continually developed more effective methods to treat periodontal disease, but these treatments are dependent upon the patient seeking treatment by an appropriate party, usually a dentist.

The disease is largely silent as characterized by an absence of symptoms, much like high blood pressure. For example, there may or may not be bleeding or pus around the teeth. Advanced cases frequently cause systemic problems due to the massive amount of infection present.

The sole cause of periodontal disease is dental plaque which is a bacterial substance present in the mouth. However, due to the fact that every person has a different genetic background, some people are resistant to the disease while others are extremely prone. Additionally, the problem is enhanced by infrequent dental visits and non-diagnosis of the disease.

The periodontal probe is the only significant clinical tool used for checking a person's periodontal disease status. Conventional probes have either lines or marks to indicate the depth that the probe penetrates between the tooth and the gum. A non-diseased condition is reflected by a probe depth of from 1 to 3 millimeters between the tooth and gum. A deeper insertion indicates a problem, and the depth of the insertion corresponds to the amount of bone loss. Additionally, at a probe depth of 5 millimeters, it is virtually impossible to remove calculus or foreign debris from the roots of diseased teeth. At this critical depth, a patient will likely require surgical treatment which may be costly and uncomfortable.

Conventional periodontal probes having uncolored lines or marks indicating probe depth are difficult to see when used by a dentist. Because of the inability of conventional probes to clearly and accurately measure probe depth, dentists occasionally insert a flexible gutta percha point into periodontal pockets and take a radiograph to see the anatomy of the pocket, since gutta percha can be visualized on x-ray. This procedure may be used to decide if surgical treatment is required. This procedure is obviously very tedious and exposes the patient to additional x-rays.

A primary or first stage of periodontal disease is gingivitis which is detected by eliciting any bleeding while probing. One method of diagnosis of gingivitis is the use of pieces of balsa wood which are sold, for example, by Johnson & Johnson under the trademark "STIM-U-DENT." One problem with the use of pieces of balsa wood is that they are too large and rough to be used accurately.

Further, many back teeth have two or more roots. Frequently, bone is lost during periodontal disease between the roots. This area of the tooth where the roots divide is referred to as the "furcation." When bone is lost between roots, there exists a "furcation involvement." The depth of furcation involvement is of paramount importance in determining the prognosis and required treatment of the tooth. Without a means of accurately assessing the depth of these areas, it is difficult for dental practitioners to make a proper diagnosis, particularly with respect to a surgery or no surgery decision.

The dental instrument art lacks a probe that the dental professional can use to easily diagnose periodontal disease and gingivitis and simultaneously be used to easily determine if surgical treatment is likely required. In addition, a method for routinely diagnosing and monitoring periodontal disease and gingivitis, and at the same time assessing if surgical treatment is likely required does not currently exist.

SUMMARY OF THE INVENTION

It is therefore an object of the present invention to provide a periodontal probe useful for the early detection of periodontal disease and gingivitis.

It is also an object of the present invention to provide a periodontal probe useful to determine if surgical treatment is likely required.

Another object is to detect furcation involvement by means of a periodontal probe which has the ability to easily assess the depth of furcation involvement in all directions, thus enabling the dental practitioner to determine if surgical treatment is likely required in a manner not previously possible, specifically because conventional probes cannot clearly indicate the exact probe depth where surgical treatment is generally required.

Yet another object is the diagnosis of gingivitis by demonstrating the bleeding point.

Another object of the invention is to provide an easy to use, disposable periodontal probe for the use of dentists and physicians to routinely check for periodontal disease and to determine if surgical treatment is likely required.

It is still another object of the invention to provide a method for the detection of periodontal disease.

In accordance with one aspect of the present invention these objects are achieved by a periodontal probe, comprising:

(a) an elongated member having a distal end with a tip thereon;

(b) the distal end being tapered to the tip and having a plurality of condition indicating portions comprising:

(1) a first portion indicating a non-diseased condition disposed between the tip and a second portion, (2) the second portion indicating a moderately diseased condition disposed between the first portion and a third portion;

(3) the third portion indicating a diseased condition wherein surgery is required;

(4) a narrow line being positioned in the second portion between the first and third portions, with the narrow line defining a boundary between two areas, a first area indicating a diseased condition likely not requiring surgery located between the first portion and the narrow line and a second area indicating a diseased condition likely requiring surgery located between the narrow line and the third portion.

In accordance with another aspect of the present invention these objects are achieved by a method for diagnosing periodontal disease comprising the steps of:

(a) inserting a periodontal probe, at the juncture between a tooth and gum, comprising:

an elongated member having a distal end with a tip thereon;

the distal end being tapered to the tip and having a plurality of condition indication portions comprising:

(1) a first portion indicating a non-diseased condition disposed between the tip and a second portion, (2) the second portion indicating a moderately diseased condition disposed between said first portion and a third portion;

(3) the third portion indicating a diseased condition wherein surgery is required;

(4) a narrow line being positioned in the second portion between the first and third portions, with the narrow line defining a boundary between two areas, a first area indicating a diseased condition likely not requiring surgery located between the first portion and the narrow line and a second area indicating a diseased condition likely requiring surgery located between the narrow line and the third portion.

(b) examining the distal end and ascertaining which of the three portions or narrow line is visible at the juncture;

(c) removing the periodontal probe from between the tooth and gum; and (d) repeating steps (a) through (c) at least once.

BRIEF DESCRIPTION OF THE DRAWINGS

Other objects, features and advantages of the present invention will become apparent from the following detailed description and accompanying drawings wherein.

DETAILED DESCRIPTION OF THE PREFERRED EMBODIMENTS

Figure 1:
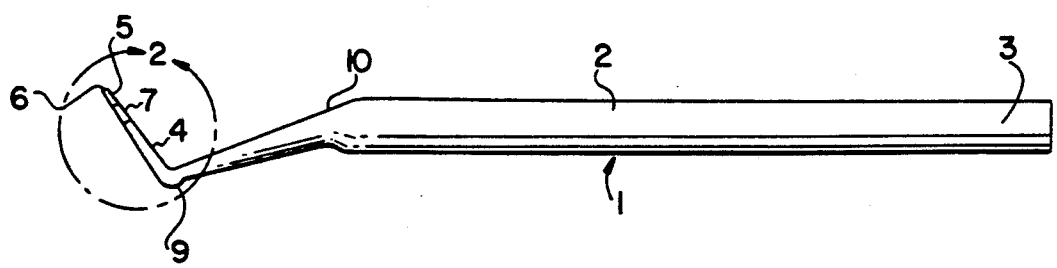
FIG. 1 is a side plan view of a periodontal probe.

Referring to FIG. 1, there is shown a periodontal probe 1 comprising an elongated member 2. The elongated member 2, which is of FDA compliant non-toxic plastic material suitable for oral use, has a proximal end 3 and a distal end 4. Such material can be polypropylene homo-polymer, polypropylene co-polymer, high density polyethylene homo polymer or polyethylene co-polymer or polybutylene terephthalate or nylon or ABS (acrylonitrile, butadiene, styrene, ter polymer) or acrylic multipolymer, or polymer blends or alloys; which may incorporate a 5% to 45% talcum, mica or fiberglass filler. In the preferred embodiment the material is either 40% talcum filled polypropylene homo polymer or polybutylene terephthalate, with filled polypropylene homo polymer being the preferred of the two. In order to obtain the desired flexibility, material is used which has a flex modulus (tangent) in the range of about $1.3-9.2 \times 10^5$ p.s.i. with a preferred modulus of about $5.1 \times 10^5$ p.s.i.

The distal end 4, which is flexible, has a first portion 5, indicating a non-diseased condition, which is disposed between a tip 6 and a second portion 7. The second portion 7 indicates a moderately-diseased condition which may require surgery and is disposed between the first portion 5 and a third portion 8.

The third portion 8 indicates a diseased condition wherein surgery is required and is disposed adjacent to the second portion 7. A narrow line 9 is located at about the midpoint of the second portion 7 and indicates that a diseased condition exists that likely requires surgery.

The elongated member 2 has a first bend 10 disposed between the proximal end 3 and the distal end 4. A second bend 9 is disposed between the tip 6 and the first bend 10. It should be noted that the elongated member can have any number of bends at any desired angle which can achieve the desired function of enabling the dental probe to be held by hand and enabling the easy insertion of the distal end at the juncture between a tooth and gum. The purpose of the bends in the elongated member is to offset the distal end at an angle which facilitates easy insertion and examination of the dental probe. A desired embodiment is achieved when the first bend is directed downward forming an obtuse angle at the bottom side of the elongated member and the second bend is directed upward forming an obtuse angle at the top side of the elongated member.

Figure 2:
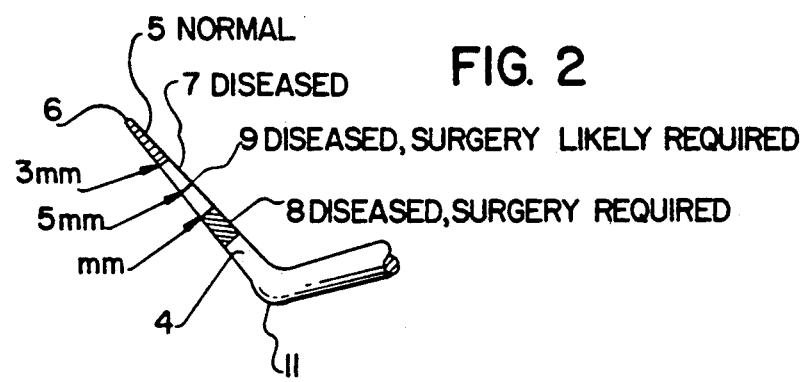
FIG. 2 is a magnified view of a section of the distal end of the periodontal probe shown in FIG. 1.

Referring to FIG. 2 there is shown a magnified view of a section of the flexible distal end of the dental probe shown in FIG. 1 in which the first portion 5 is about 3 millimeters in length, the second portion 7 is about 4 millimeters in length, and the third portion 8 is about 3 millimeters in length, all portions together extending a length of about 10 millimeters from the tip 6. Additionally, the narrow line 9 is disposed about 5 millimeters from the tip 6, at approximately the midpoint of the second portion 7. When the distal end is inserted at the juncture between a tooth and gum up to a length of about 3 millimeters, the first portion remains visible indicating a non-diseased condition. Insertion of the distal end beyond about 3 millimeters but less than about 5 millimeters results in the second portion being partly visible indicating a diseased condition not likely requiring surgery. Insertion of the distal end beyond about 5 millimeters but less than about 7 millimeters indicates a diseased condition that likely requires surgery. Insertion of the distal end beyond about 7 millimeters indicates a severely diseased condition requiring surgery. FIG. 2 shows the second portion 7 extending from about the 3 millimeter mark to about the 7 millimeter mark, shows the narrow line 9 at the 5 millimeter mark and the third portion 8 extending from the 7 millimeter mark to the 10 millimeter mark.

Additionally, the first, second and third portions can be contrastingly color-coded to aid the user when attempting to ascertain which of the three portions is visible during the examination. The narrow line can be contrastingly color-coded with the second portion to highlight if the narrow line is visible during examination. In one example of colorcoding, the first portion can be colored green, the second portion can be colored white, the third portion can be colored red and the narrow line red. In effect, any three colors which contrast each other can be chosen. The color is obtained by the use of a non-toxic compliant ink.

The dental probe shown in FIG. 1 is about 5 inches in length, but can be any length that is convenient for handheld use. The dental probe shown in FIG. 2 tapers from the first bend 10 to the tip 6 which has a width of about ½ of a millimeter. The tip at the distal end can have any width that is suitable for inserting the distal end at the juncture between a tooth and gum.

The present invention also includes a method for diagnosing periodontal disease. This method includes the steps of inserting a dental probe at the juncture between a tooth and gum. The distal end is then examined to ascertain which of the three portions is visible at the juncture and ultimately whether a diseased or nondiseased condition exists. Furthermore, if the second portion is visible the distal end can be further examined to determine if the narrow line is visible. This method creates a simple yes-no situation for determining disease status as well as whether surgery is, may be, or is not required. The dental probe is then removed from between the tooth and gum and gently inserted at another juncture. This process can be repeated until all the tooth/gum junctures are examined.

Figure 3:
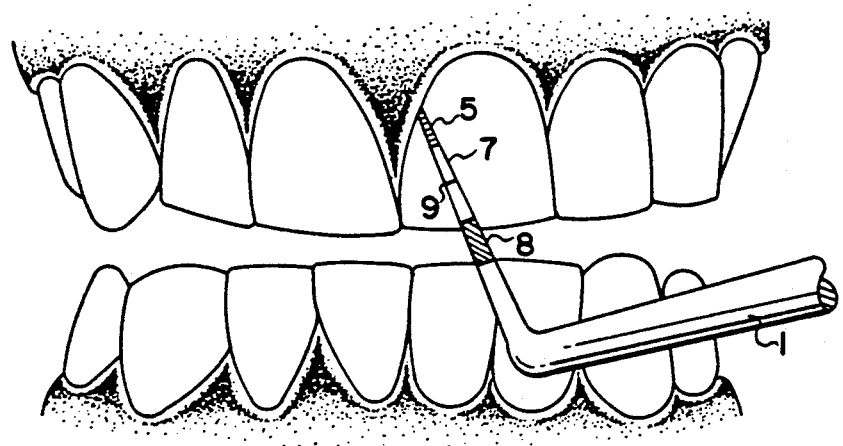
FIG. 3 is a perspective view of a periodontal probe inserted at the juncture between a healthy tooth and gum.

Referring to FIG. 3, there is shown the dental probe 1 inserted at a juncture between a tooth and gum. The first portion 5 remains visible indicating a non-diseased condition. The second portion 7, narrow line 9 and third portion 8 are also visible as a result of the dental probe not being able to penetrate at least about 3 millimeters.

Figure 4:
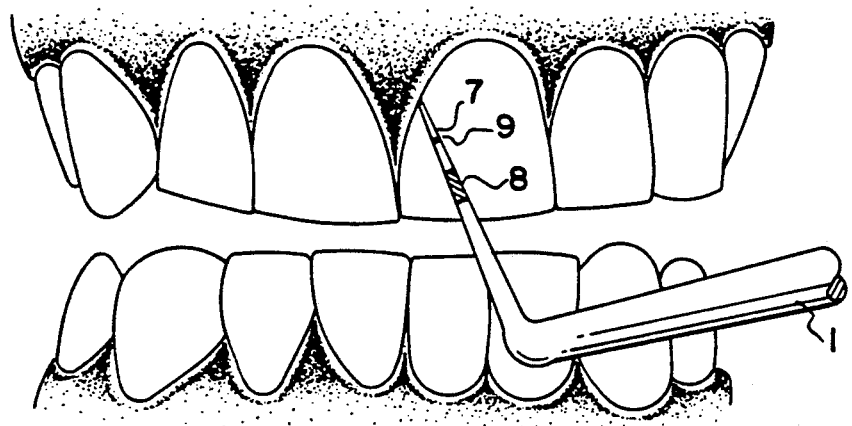
FIG. 4 is a perspective view of a periodontal probe inserted at the juncture between a diseased tooth and gum which does not likely require surgery.

Referring to FIG. 4, there is shown the dental probe 1 inserted at a juncture between a tooth and gum in which the second portion 7, narrow line 9 and third portion 8 remain visible indicating a diseased condition not likely requiring surgery.

Figure 5:
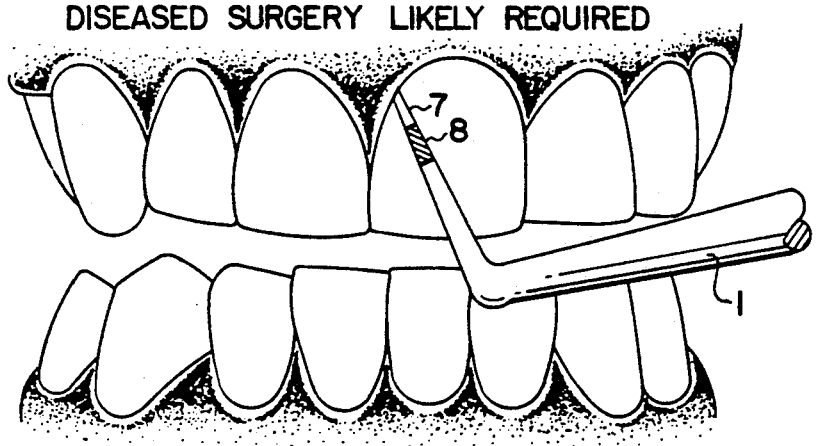
FIG. 5 is a perspective view of a periodontal probe inserted at the juncture between a diseased tooth and gum which likely requires surgery.

Referring to FIG. 5, there is shown the dental probe 1 inserted at a juncture between a tooth and gum in which only part of the second portion 7 and the entire third portion 8 remain visible indicating a diseased condition likely requiring surgery.

Figure 6:
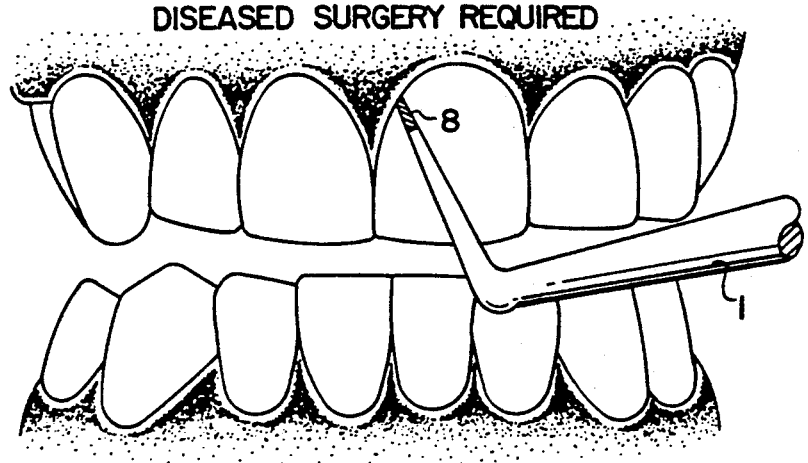
FIG. 6 is a perspective view of a periodontal probe inserted at the juncture between a diseased tooth and gum which requires surgery.

Referring to FIG. 6, there is shown the dental probe 1 inserted at a juncture between a tooth and gum in which only the third portion 8 remains visible indicating a diseased condition requiring surgery.

The method of detecting gingivitis is substantially the same in that the probe is used to detect any bleeding. The Examiner can ascertain whether the depth of or furcation involvement exceed the critical 5 millimeter mark.

The present method can also include the step of coding the three portions with contrasting colors for ease of identification. In addition, the narrow line can be color coded to contrast with the second portion increasing its visibility. The specific portion of the distal end visible for each tooth and gum area examined can be charted with an examination chart showing the teeth and gums in their position relative to one another. In this method, the entire mouth can be charted to determine where the troubled spots are. Additionally, the chart can be used to indicate whether or not bleeding occurred. Therefore, at a glance, the patient can see from the chart where the pockets are or where bleeding occurred. A person using this method can conceivably chart individual patients after a period of time to see what changes may have occurred following either professional care or self treatment, for example, by improved tooth brushing and dental flossing. The probe as stated above, can be made from plastic or metal and can be disposable, depending upon the desired use.

While several embodiments of the invention have been described, it will be understood that it is capable of still further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A periodontal probe, comprising:
   a) an elongated member having a distal end with a tip thereon; and
   b) said distal end being tapered to said tip and having a plurality of condition indicating portions comprising:
      (1) a first portion indicating a nondiseased condition disposed between said tip and a second portion,
      (2) said second portion indicating a moderately-diseased condition disposed between said first position and a third portion,
      (3) said third portion indicating a diseased condition wherein surgery is required,
      (4) a narrow line being positioned in said second portion between said first portion and said third portion, said narrow line defining a boundary between two areas, a first area indicating a diseased condition likely not requiring immediate surgery located between said first portion and said narrow line, and a second area indicating a diseased condition likely to require surgery located between said narrow line and said third position.

2. The periodontal probe according to claim 1, wherein said first portion is about 3 millimeters in length, said second portion is about 4 millimeters in length, said third portion is about 3 millimeters in length and said narrow line is located about 5 millimeters from said distal end.

3. The probe according to claim 1, wherein said first portion, said second portion and said third portion are contrastingly color coded.

4. The periodontal probe according to claim 3, wherein said first portion is green, said second portion is white, and said third portion is red.

5. The periodontal probe according to claim 1, wherein said narrow line and said second portion are contrastingly color coded.

6. The periodontal probe according to claim 5, wherein said narrow line is red and said second portion is white.

7. The periodontal probe according to claim 1, wherein said probe is disposable.

8. The periodontal probe according to claim 1, wherein at least said probe tip is a plastic containing a filler selected from a group consisting of talcum, mica and fiberglass.

9. The periodontal probe according to claim 8, wherein said filler comprises between about 5% to 45% of said plastic.

10. The periodontal probe according to claim 1 wherein said probe is of flexible plastic.

11. The periodontal probe according to claim 10, wherein said plastic is selected from a group consisting of polypropylene homo-polymer and polybutylene terephthalate.

12. A periodontal probe according to claim 10, wherein said plastic is selected from a group consisting of polypropylene homo-polymer, polypropylene co-polymer, high density polyethylene homo-polymer, polyethylene co-polymer, polybutylene terephthalate, nylon or ABS (acrylonitrile, butadiene, styrene, ter polymer) and acrylic multipolymer.

13. A periodontal probe according to claim 12 including a filler selected from the groups consisting of talcum, mica and fiberglass.

14. A periodontal probe according to claim 10, wherein said plastic is polypropylene homo-polymer containing a talcum filler.

15. A periodontal probe according to claim 14, wherein said filler is about 40%.

16. A periodontal probe according to claim 10, wherein said plastic has a flex modulus (tangent) of about $1.3-9.2 \times 10^5$ p.s.i.

17. A periodontal probe according to claim 10, wherein said plastic has a flex modulus (tangent) of about $5.1 \times 10^5$ p.s.i.

18. A periodontal probe according to claim 1, wherein said probe is metal.

19. The periodontal probe according to claim 1, wherein said elongated member has a first bend disposed between a proximate end and a distal end.

20. The periodontal probe according to claim 19, wherein said distal end has a second bend disposed between said distal end tip and said first bend.

21. The periodontal probe according to claim 20, wherein said first bend forms an obtuse angle at a bottom side of said elongated member.

22. The periodontal probe according to claim 20, wherein said second bend forms an obtuse angle at a top side of said elongated member.

23. A method for diagnosing periodontal disease comprising the steps of:
  (a) inserting a periodontal probe, at a juncture between a tooth and gum, comprising:
    an elongated member having a distal end with a tip thereon;
    said distal end being tapered to said tip and having a plurality of condition indicating portions comprising:
      (1) a first portion indicating a non-diseased condition disposed between the tip and a second portion,
      (2) the second portion indicating a moderately-diseased condition disposed between said first portion and a third portion;
      (3) the third portion indicating a diseased condition wherein surgery is required;
      (4) a narrow line being positioned in the second portion between the first and third portions, with the narrow line defining a boundary between two areas, a first area indicating a diseased condition likely not requiring surgery located between the first portion and the narrow line and a second area indicating a diseased condition likely requiring surgery located between the narrow line and the third portion.
  (b) examining the distal end and ascertaining which of the three portions or narrow line is visible at the juncture;
  (c) removing the periodontal probe from between the tooth and gum; and
  (d) repeating steps (a) through (c) at least once.

24. The method according to claim 23 further comprising the step of coding said three portions with contrasting colors.

25. The method according to claim 23 further comprising the step of coding said second portion and said narrow line with contrasting colors.

26. The method according to claim 23 further comprising the step of charting the specific portion visible for each tooth and gum area examined.

27. The method according to claim 23 including bending said tip in tortuous pockets.

28. The method according to claim 23 including locating furcation involvement.

29. The method according to claim 23 including forming at least said tip of a talcum filled polypropylene homo-polymer.

30. The method according to claim 23 including forming at least said tip of a polybutylene terephthalate.

31. The method of claim 23 including forming the tip with a plastic having a flex modulus (tangent) of about $1.3-9.2 \times 10^5$ p.s.i.

32. The method of claim 23 including forming the tip with a plastic having a flex modulus (tangent) of about $5.1 \times 10^5$ p.s.i.

33. The method of claim 23 including eliciting any bleeding while probing to diagnose gingivitis.

34. The method of claim 23 including forming the distal end with a flexible plastic.

35. The method of claim 23 including forming the probe with a metal.

* * * * *